United States Patent
De Lange et al.

(10) Patent No.: US 7,042,978 B2
(45) Date of Patent: May 9, 2006

(54) EXAMINATION OF MATERIAL SAMPLES

(75) Inventors: Roelof De Lange, Falmer (NL); Bruno A. R. Vrebos, Falmer (NL)

(73) Assignee: Panalytical B.V., Ea Almelo (NL)

( * ) Notice: Subject to any disclaimer, the term of this patent is extended or adjusted under 35 U.S.C. 154(b) by 0 days.

(21) Appl. No.: 10/482,562

(22) PCT Filed: Jun. 20, 2002

(86) PCT No.: PCT/IB02/02402

§ 371 (c)(1),
(2), (4) Date: Jun. 8, 2004

(87) PCT Pub. No.: WO03/002995

PCT Pub. Date: Jan. 9, 2003

(65) Prior Publication Data

US 2004/0234029 A1    Nov. 25, 2004

(30) Foreign Application Priority Data

Jun. 29, 2001 (EP) ................................. 01202511

(51) Int. Cl.
*G01N 23/20* (2006.01)
(52) U.S. Cl. .......................... 378/79; 378/83
(58) Field of Classification Search ............ 378/44–50, 378/70–90
See application file for complete search history.

(56) References Cited

U.S. PATENT DOCUMENTS

| | | | | |
|---|---|---|---|---|
| 3,919,548 A | * | 11/1975 | Porter ........................ | 378/45 |
| 4,959,848 A | * | 9/1990 | Parobek ........................ | 378/46 |
| 4,961,502 A | * | 10/1990 | Griffiths ....................... | 206/455 |
| 4,962,517 A | | 10/1990 | Koga | |
| 5,060,247 A | | 10/1991 | Watanabe | |
| 5,754,621 A | * | 5/1998 | Suzuki et al. ................. | 378/57 |
| 5,781,608 A | * | 7/1998 | Tomie et al. ................ | 378/119 |

FOREIGN PATENT DOCUMENTS

| | | |
|---|---|---|
| EP | 0 014 580 | 8/1980 |
| JP | 57 131042 | 8/1982 |
| JP | 62177845 | 8/1987 |

OTHER PUBLICATIONS

Notification of Transmittal of Intenational Search Report, International Application No. PCT/IB 02/02402, Jan. 21, 2003.

* cited by examiner

*Primary Examiner*—David V. Bruce
*Assistant Examiner*—Hoon Song
(74) *Attorney, Agent, or Firm*—Blakely Sokoloff Taylor & Zafman

(57) ABSTRACT

A device (1; 1*a*) for the examination of at least one material sample (3; 3*a*, 3*b*, 3*c*) which can be inserted into the device (1; 1*a*) and is irradiated by means of electromagnetic waves (4), notably X-rays; in the measuring position the material sample (3; 3*a*, 3*b*, 3*c*) can be subjected to irradiation by means of the electromagnetic waves (4) and during a change of sample the beam path (4) can be interrupted by means of a closure element (8) which can be moved into the beam path. The device is constructed in such a manner that the closure element (8) is provided with a reference sample (9) on its side which faces the rays (4) in a manner such that a reference measurement can be performed thereon during a change of sample.

16 Claims, 3 Drawing Sheets

EXAMINATION OF MATERIAL SAMPLES

Figure 1:
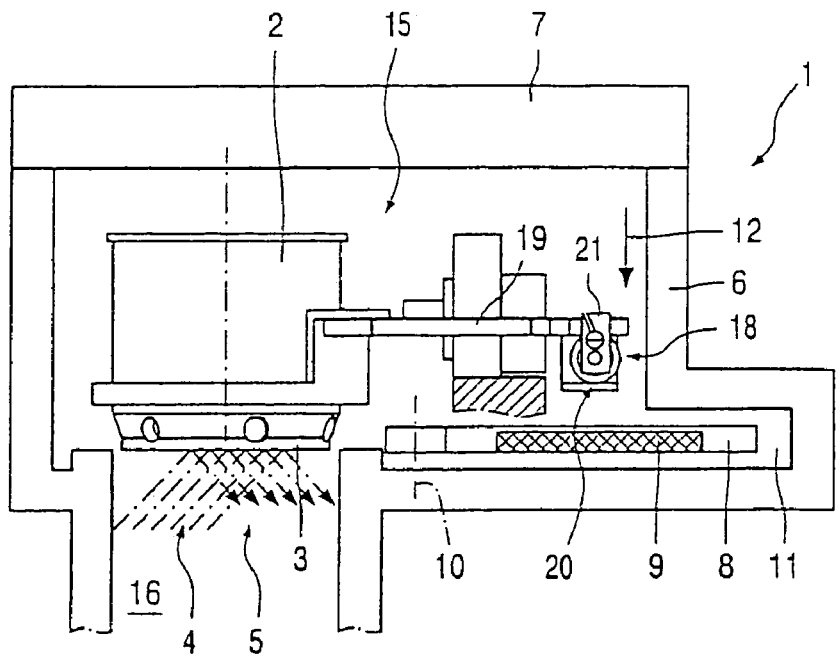

The present patent application is a non-provisional application of International Application No. PCT/IB02/02402, filed Jun. 20, 2002.

The invention relates to a device for the examination of one or more insertable material samples.

Either individual samples can be inserted in devices of this kind, in which case a change of sample has to be carried out by a user, or a plurality of samples can be arranged, for example, on a turntable so that a change of sample can be carried out either by the user by exchanging the samples on the turntable or by controlled further rotation of the turntable in the device. A change of sample can thus take place in two different ways in devices of this kind.

A change of sample is then accompanied by a disturbance of the measuring conditions. For example, when the apparatus is opened a protective gas atmosphere or a vacuum is disturbed; moreover, the temperature changes. When the radiation source, for example, the X-ray source, must be switched off during the change of sample, the service life of will become shorter. The stability of the emission of radiation cannot be sustained for a number of measurements of different samples.

It is an object of the invention to carry out the change of sample in such a manner that the measuring conditions are substantially identical for each of the measured samples.

During the change of sample in the device in accordance with the invention a reference measurement can be carried out each time between two samples. This enables optimization of the device such, that the same conditions prevail for different samples. For example, the intensity of the radiation source can be readjusted or the residual gas pressure in the measuring chamber can be changed during the measurement of the reference sample. The same holds, for example, for the orientation of the detector, the sample and the radiation source relative to one another, so that each measurement of the reference sample yields a substantially identical measuring result, thus ensuring that the same measuring conditions also occur for the measurements of the material samples which are performed between the measurements of the reference sample.

Because the closure element is movable in the beam path, moreover, it is ensured that the radiation source can continue to operate in a stable manner also during a (manual) change of sample.

During the change of sample it is particularly advantageous to keep the reference sample of the closure element as exactly as possible in the position in which a material sample to be measured is situated in the functional state. When the closure element is constructed so as to be very thin, keeping the position can be realized by pivoting the closure element underneath the sample present in the functional position so that it can be exposed to the radiation previously incident on the sample. When the thickness of the material of the closure element is greater, there may be provided a lifting mechanism which displaces the relevant material sample perpendicularly to the longitudinal direction of the reference sample while the closure element is open, thus ensuring that the material sample to be examined reaches exactly the position occupied by the reference sample of the closure element during the change of sample.

A protective function can be realized for the reference sample notably when the closure element supporting said reference sample is arranged so as to be pivotable about an axis extending perpendicularly to its longitudinal plane. In the open condition the reference sample can then be stored so as to be freely suspended in a slit-shaped and inaccessible space. It is impossible for the user to invade this space.

Reproducible positioning of the closure element and the reference sample accommodated therein is obtained when the closure element is not only separated from the chamber with the radiation source by way of a seal, but also rests on a fixed abutment in the closed condition.

When the closure element is movable independently of the material sample, the closure element can be closed and a measurement can be performed on the reference sample, for example, in every position of a turntable with a plurality of material samples.

It is particularly advantageous that for each change of sample a reference measurement can be carried out, thus enabling fine adjustment of the device, if necessary.

Figure 2:
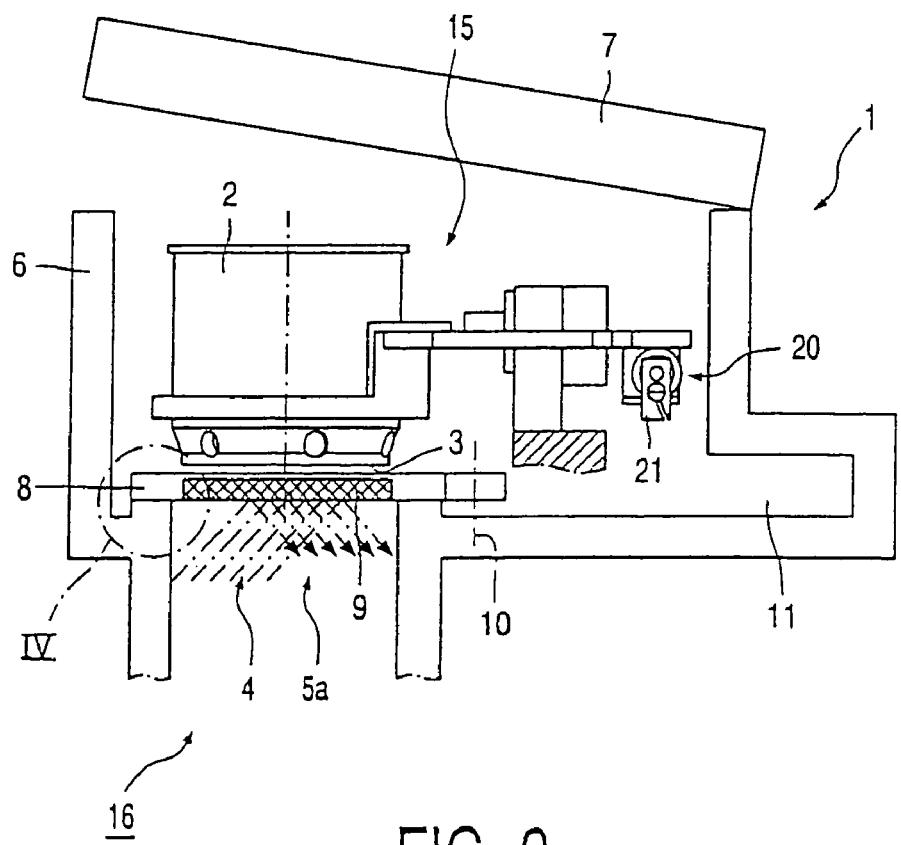
Figure 3:
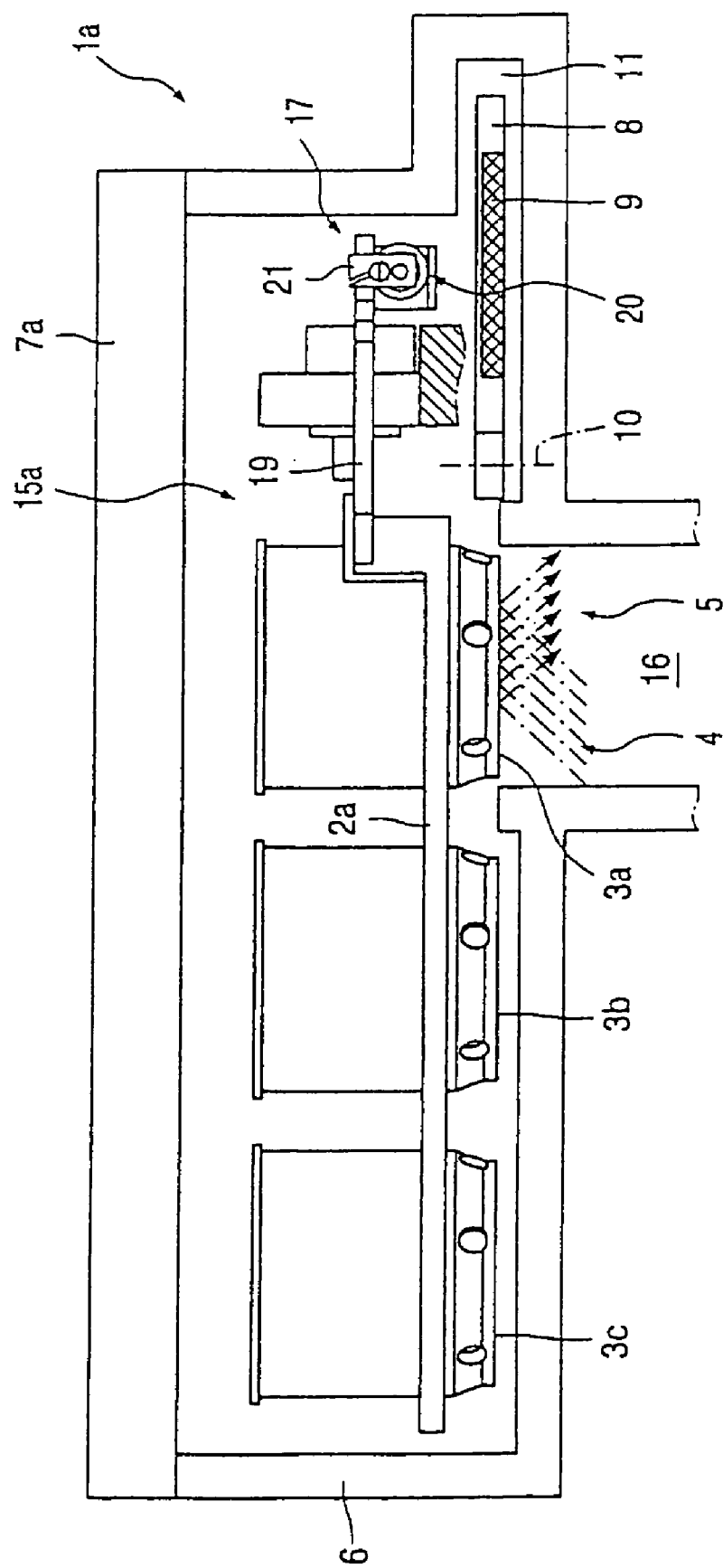
Figure 4:
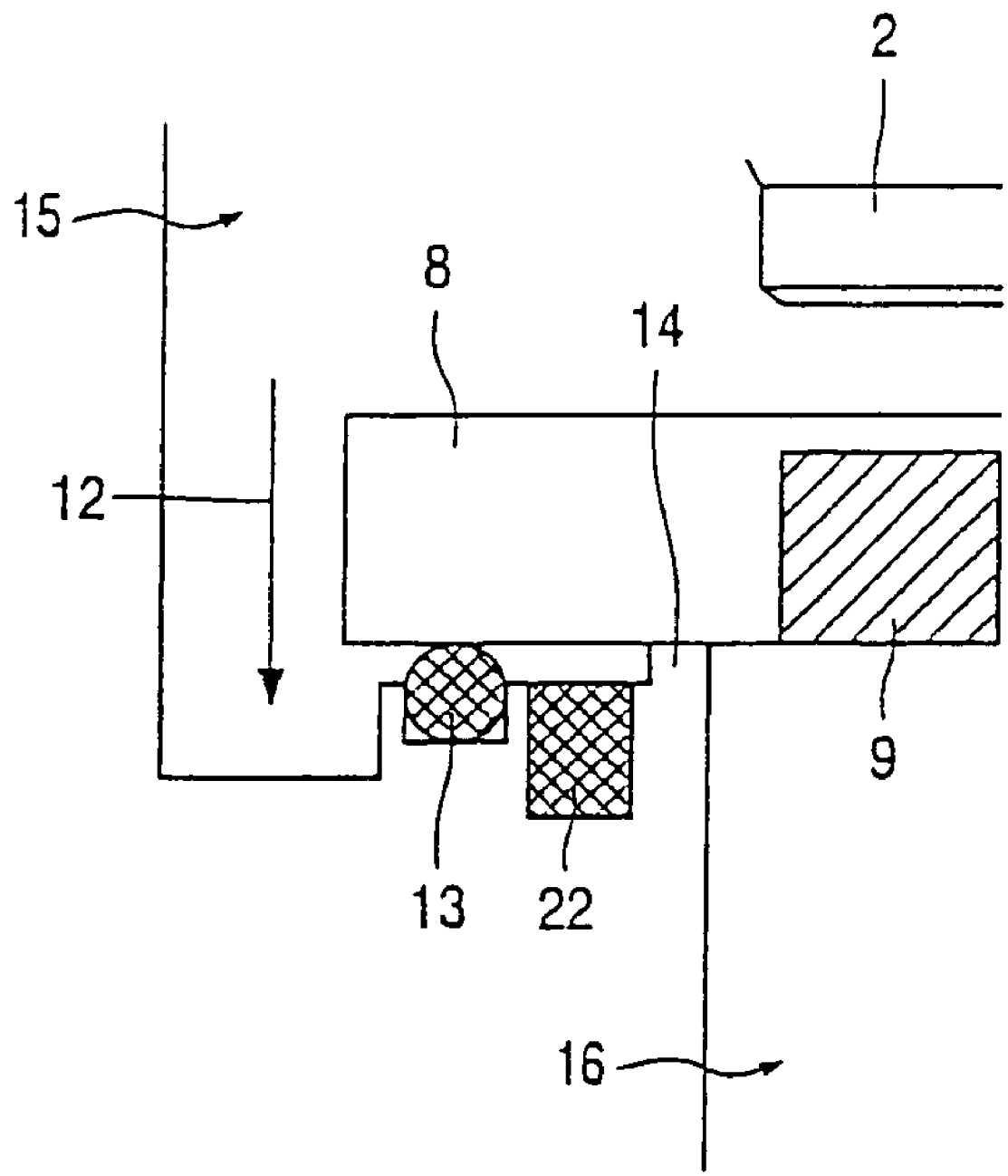

Further advantages and features will become apparent from the embodiment of the invention as shown in the drawing. In the drawing:

FIG. 1 is a diagrammatic cross-sectional view of a device in accordance with the invention, that is, of the vicinity of the sample holder during the analysis of a material sample, FIG. 2 is a view similar to that of FIG. 1 during a change of sample, FIG. 3 is a view similar to that of FIG. 1 of a device provided with a sample changer, and FIG. 4 is a detailed representation of the detail IV in FIG. 2.

A first embodiment (FIG. 1) of the device 1 includes a sample holder 2 which may be provided with an exchangeable material sample 3. The material sample 3 can be examined in the device 1 by irradiation by means of electromagnetic waves 4, notably X-rays which are emitted by an X-ray source (not shown). The reflected rays (Bragg reflection on grid planes) as well as the rays 5 produced by secondary processes (fluorescence) or scattering are then analyzed in a detector (not shown).

The entire device 1 is shielded from the environment by means of fixed walls 6, for example, walls made of steel, as well as by means of a wall section 7 which can be opened, that is, notably a lid section. Because the wall section 7 can be opened, the sample holder 2 can be accessed, for example, for a change of sample.

The device 1 also includes a so-called shutter 8, that is, a closure element which can be inserted so as to interrupt the path of the rays 4. The closure element 8 is provided with a reference sample 9 which can be moved to the position of the material sample 3 upon a change of sample during which the material sample 3 is removed from the measuring position shown in FIG. 1. To this end, the complete closure element 8 is pivotable about an axis 10 which extends perpendicularly to the longitudinal plane of the closure element 8. In the measuring position of the material sample 3 the closure element 8 is in a deflected position, in which it is accommodated in a pocket 11 of the device in such a manner that the reference sample 9 is situated at a small distance from a wall section and hence is protected against mechanical damage.

During the change of sample (FIG. 2) the closure element 8 is moved into the beam path 4 so that the rays 4 are incident on the reference sample 9 in the same way as on the material sample 3 during the measurement thereof. Analogously to the rays 5 which emanate from a material sample 3 so as to travel towards the detector, in this position a number of rays 5a from the reference sample 9 is conducted to the detector so as to be measured.

In order to ensure that during the change of sample in conformity with FIG. 2 the reference sample 9 is situated in exactly the same position as a material sample 3 in the measuring position shown in FIG. 1, the closure element 8 is capable of performing, in addition to the pivoting motion shown illustrated by FIG. 1 and FIG. 2, an additional stroke in the direction of the arrow 12, for example, in that an underpressure acts on the closure element 8 and pulls it downwards. A magnetic force, exerted by electromagnetic coils 22 on the closure element 8 which may consist, for example, of stainless steel, can also be used for the displacement perpendicularly to its longitudinal plane, that is, in the direction of the arrow 12.

FIG. 4 is a detailed view which shows that in the lowered position the closure element 8 bears on a seal 13, for example, a circular sealing ring, and on the other hand still bears on a rigid abutment 14. Because the closure element 8 is not only maintained against the seal 13 but always bears also on the rigid abutment 14 in the final position during the change of sample, it is ensured that the reference sample 9 can always be maintained in exactly the same position and hence that the reference measurements during the change of sample always takes place under exactly the same geometrical conditions. This offers reproducibility of the measuring results. In addition to the exact geometrical reproducibility, further parameters, such as pressure, temperature, residual gas composition in the propagation room of the rays 4 and 5 from a sample 3 to be examined or 5a from the reference sample 9, can also be kept constant, because prior to the change of sample the closure element 8 can always be moved to its closing position shown in FIG. 4, so that the radiation propagation space 16 is sealed from the external sample chamber 15. Air can then be admitted to the sample chamber 15 by opening the lid 7 so as to perform an exchange of the samples 3. The radiation propagation space 16 is not affected thereby.

In a second embodiment as shown in FIG. 3 a sample holder 2a is provided with a plurality of samples 3a, 3b, 3c which can be exchanged and may all be arranged, for example, on a turntable 2a. Consequently, a change of sample can be realized on the one hand by turning the turntable so that the positions of the samples 3a, 3b, 3c are interchanged. It is also possible to open the lid 7a and to exchange one or more of the material samples 3a, 3b, 3c.

A typical turntable comprises, for example, up to 12 different material samples 3a, 3b, 3c.

During both types of change of sample the closure element 8 can be inserted into the beam path 4 in order to close the radiation propagation chamber 16 and to readjust the X-ray source and the detector.

Because the closure element 8 has a radiation sealing effect, a radiation source can continue to operate in the closed condition of the closure element, so that the operating parameters of the radiation source are not subject to change. The service life of a radiation source, for example, an X-ray source, is thus significantly prolonged. Moreover, the constancy of the measuring conditions is ensured, because a starting up-phase of the radiation source after intermediate switching off can be dispensed with.

It may also be useful to close the radiation propagation chamber 16 by way of the closure element 8 also during a change of sample which takes place by rotating the turntable further and exchanging the samples 3a, 3b, 3c against one another, thus adapting the adjustment of the radiation source and the detector relative to one another in such a manner that they are always in the same relative position with respect to each other. This can be realized, for example, by way of an intensity measurement of the rays 5 incident on the detector. To this end, the closure element 8 is in any case movable independently of the sample holder 2a in the form of a turntable, so that it can be closed each time between two samples 3a, 3b, 3c.

In order to ensure that the sample 3, 3a, 3b, 3c to be examined can always be positioned exactly in the same position as the reference sample 9, that is, in devices 1 with only one insertable material sample 3 as well as in devices 1a with a plurality of insertable material samples 3a, 3b, 3c, there is provided a displacement device 17 which acts on the sample holder 2, 2a in such a manner that the material sample 3, 3a, 3b, 3c can be moved to the position occupied by the reference sample 9 during the change of sample. The displacement device 17 includes a lifting mechanism 18 which is connected to the sample holder 2 or 2a via an extension arm 19 which extends parallel to the closure element. The displacement device 17 can be dispensed with when the closure element 8 is constructed so as to be extremely thin; this may be the case, for example, when the overall device 1 operates with a helium atmosphere so that no significant pressure differences occur between the radiation propagation chamber 16 and the probe chamber 15.

However, when a vacuum is to be created in the radiation propagation chamber 16 while air is admitted to the sample chamber 15 (see FIG. 2), a significant pressure is exerted on the closure element 8 in the closed position, so that it should be constructed so as to be comparatively thick. The exactness of the correspondence of the position of the reference sample 9 with that of the relevant sample 3, 3a, 3b, 3c to be measured can be decisively improved by means of a displacement mechanism 17, because this mechanism enables variation of the position in height of the sample 3, 3a, 3b, 3c in the open condition of the closure element 8 (FIG. 1, FIG. 3) in such a manner that the sample reaches the same level as that at which the front face of the reference sample 9 of the closure element 8 which faces the beam path 4 is situated during the change of sample. The lifting mechanism 18 operates perpendicularly to the longitudinal plane of the material sample 3, 3a, 3b, 3c, for example, in that a drive element 21 is movable along a circular path 20 in such a manner that it takes along the arm 19.

The more exact the correspondence of the positions of the reference sample 9 and the samples 3, 3a, 3b, 3c to be measured, the more exact the adjustment of the radiation source and the detector, performed on the reference sample 9, can be transferred to the material samples 3, 3a, 3b, 3c.

Optimum results can be achieved when, in the case of a change of sample between several samples 3a, 3b, 3c of a sample changer 2a in the closed condition of the lid 7a as well as in the case of a change of a single sample 3 of a single sample holder 2, the closure element 8 is moved into the beam 4 during the change of sample and readjustment of the device 1 or 1a is performed on the basis thereof. Such a reference measurement can be carried out between each time two samples 3, 3a, 3b, 3c.

Overall it is thus possible to carry out reference measurements during each type of change of sample; the beam 4 is then always reliably shielded from the environment 15 or 15a by the closure element 8, so that the lid 7, 7a may be opened without risk. The measuring environment thus remains the same in any case, that is, notably the pressure, the temperature and the gas composition in the radiation propagation chamber 16.

The reference sample 9 is built into the closure element 8 and is, therefore, insensitive to maintenance; the protected position in the pocket 11 also contributes thereto. The reference sample 9 and the relevant material sample 3, 3a, 3b, 3c can be measured in exactly the same position; the reproducible position of the reference sample 9 on the fixed abutment 14 notably contributes thereto.

The closure element in an alternative embodiment (not shown) comprises several different reference samples and, for example, additionally an open window in order to enable measurement of the material samples 3 therethrough.

The invention claimed is:

1. A device for the examination of at least one material sample, comprising:
   a sample chamber;
   a sample holder in the sample chamber for holding a material sample in a measuring position;
   an X-ray source for irradiating the material sample with X-rays; and
   a closure element for sealing the sample chamber moveable between a closed position sealing the chamber and a measuring position in which the closure element is deflected from the sealing position; and
   a reference sample mounted on the closure element;
   wherein the closure element interrupts the X-rays in the closed position, and when the closure element is in the closed position the reference sample is arranged in exactly the same position as a material sample in the measuring position.

2. The device according to claim 1, wherein the sample chamber defines an internal pocket arranged to accommodate the closure element in the measuring position wherein the internal pocket cooperates with the closure element to protect the reference sample from mechanical damage in the internal pocket within the sample chamber when the closure element is in the measuring position within the internal pocket.

3. The device as claimed in claim 1, the closure element is moved into a position in which it is situated in a beam path via a short path that extends perpendicularly to its longitudinal plane, and the closure element one of compresses and releases a resilient seal in the case of such a movement.

4. The device as claimed in claim 3, wherein in the position of the closure element in which it compresses the seal is held on a rigid abutment.

5. The device as claimed in claim 1, wherein the closure element is movable independently of one of the material sample and another material sample.

6. The device as claimed in claim 1, wherein a plurality of material samples is arranged on a turntable.

7. The device as claimed in claim 1, further comprising:
   a pocket for accommodating the reference sample in a deflected position away from a beam path for protecting the reference sample against mechanical damage.

8. The device as claimed in claim 2, further comprising:
   a pocket for accommodating the reference sample in a deflected position away from a beam path for protecting the reference sample against mechanical damage.

9. The device as claimed in claim 3, further comprising:
   a pocket for accommodating the reference sample in a deflected position away from the beam path for protecting the reference sample against mechanical damage.

10. The device as claimed in claim 4, further comprising:
    a pocket for accommodating the reference sample in a deflected position away from the beam path for protecting the reference sample against mechanical damage.

11. The device as claimed in claim 5, further comprising:
    a pocket for accommodating the reference sample in a deflected position away from a beam path for protecting the reference sample against mechanical damage.

12. The device as claimed in claim 6, further comprising:
    a pocket for accommodating the reference sample in a deflected position away from a beam path for protecting the reference sample against mechanical damage.

13. A method of operating an examination device for material samples having a sample chamber and an X-ray source, comprising:
    measuring a material sample in a measuring position by irradiating it with X-rays;
    moving the material sample out of the reference position;
    moving a closure element having a reference sample mounted thereon to a closed position in which the closure element seals the sample chamber, the closure element prevents the X-rays reaching the sample chamber; and in which a reference sample mounted to the closure element is in exactly the same position as the material sample in the measuring position; and
    measuring the reference sample by irradiating it with X-rays with the closure element having the reference sample mounted thereon in the closed position.

14. The method as claimed in claim 13, wherein the material sample to be measured can be moved each time to a position in which the reference sample of the closure element is retained in the dosed state of the closure element.

15. The method as claimed in claims 13, wherein a plurality of material samples can be arranged on a turntable and that a measurement is performed on the reference sample during each displacement of the turntable.

16. The method as claimed in claims 13, wherein the closure element is dosed during a change of sample by a user and a measurement is performed on the reference sample of the closure element while the X-ray source is in operation.

* * * * *

UNITED STATES PATENT AND TRADEMARK OFFICE
CERTIFICATE OF CORRECTION

PATENT NO. : 7,042,978 B2
APPLICATION NO. : 10/482562
DATED : May 9, 2006
INVENTOR(S) : De Lange et al.

It is certified that error appears in the above-identified patent and that said Letters Patent is hereby corrected as shown below:

Col. 6, line 49;
In Claim #16, Line 2, please delete "dosed" and insert -- closed --.

Signed and Sealed this

Twenty-seventh Day of March, 2007

JON W. DUDAS
*Director of the United States Patent and Trademark Office*